United States Patent
Clevett et al.

(10) Patent No.: US 12,121,244 B2
(45) Date of Patent: Oct. 22, 2024

(54) GUIDE APPARATUS FOR SURGICAL CUTTING TOOL

(71) Applicant: Arthrex, Inc., Naples, FL (US)

(72) Inventors: James Tyler Clevett, Bonita Springs, FL (US); Nicholas Clement Mealey, Naples, FL (US); Timothy J. Thompson, Gilbert, AZ (US)

(73) Assignee: Arthrex, Inc., Naples, FL (US)

( * ) Notice: Subject to any disclaimer, the term of this patent is extended or adjusted under 35 U.S.C. 154(b) by 400 days.

(21) Appl. No.: 17/473,175

(22) Filed: Sep. 13, 2021

(65) Prior Publication Data
US 2023/0085332 A1 Mar. 16, 2023

(51) Int. Cl.
*A61B 17/17* (2006.01)

(52) U.S. Cl.
CPC .......... *A61B 17/17* (2013.01); *A61B 17/1735* (2013.01)

(58) Field of Classification Search
CPC ... A61B 17/17; A61B 17/1735; A61B 17/151; A61B 17/1764; A61B 2017/1602
See application file for complete search history.

(56) References Cited

U.S. PATENT DOCUMENTS

| | | | |
|---|---|---|---|
| 5,035,699 A * | 7/1991 | Coates | A61B 17/155 606/86 R |
| 5,207,680 A * | 5/1993 | Dietz | A61B 17/1764 606/86 R |
| 8,114,083 B2 * | 2/2012 | Haines | A61B 17/15 606/88 |
| 8,845,643 B2 | 9/2014 | Long et al. | |
| 9,005,207 B2 | 4/2015 | Dodds et al. | |
| 9,987,024 B2 * | 6/2018 | Frey | A61B 17/1703 |
| 10,568,647 B2 | 2/2020 | Kehres et al. | |
| 2018/0085133 A1 | 3/2018 | Lavallee et al. | |

FOREIGN PATENT DOCUMENTS

| | | |
|---|---|---|
| CN | 111629674 A | 9/2020 |
| EP | 1669034 B1 | 7/2008 |
| JP | 5456678 B2 | 1/2014 |
| RU | 2583369 C2 | 5/2016 |

* cited by examiner

*Primary Examiner* — Tracy L Kamikawa
(74) *Attorney, Agent, or Firm* — Price Heneveld LLP

(57) ABSTRACT

A guide apparatus for a surgical cutting tool includes a plurality of plates arranged in parallel with a guide plane. The plates form opposing bearing surfaces spaced apart over a clearance distance that defines an opening. A sheath includes a cylindrical portion that extends along a longitudinal axis and forms an interior passage extending through cylindrical portion along the longitudinal axis. The cylindrical portion of the sheath slidably engages the opening through the clearance distance, and the interior passage of the sheath receives a rotary cutting head of the surgical cutting tool in an operating configuration.

21 Claims, 7 Drawing Sheets

GUIDE APPARATUS FOR SURGICAL CUTTING TOOL

BACKGROUND

The present disclosure generally relates to a guide apparatus for a surgical cutting tool and, more specifically, relates to a guide apparatus that aligns a surgical cutting tool with a resection or cutting site. The alignment of surgical cutting tools along cutting planes or surfaces of bones may be applied as an initial step prior to surgically attaching a prosthetic joint or device to a bone. The resection of the bone may be applied to a distal or proximal end portion forming a joint of a patient. In order to ensure a proper fit and alignment of a prosthetic device or joint for connection with the bone, the alignment of the cutting or resection plane at an appropriate angle or extent relative to the joint may be imperative. The disclosure provides for a guide apparatus and methods of operation that may assist in the effective alignment of a resection plane to improve the efficiency and ease of accomplishing various surgical operations.

SUMMARY

In various implementations, the disclosure provides for a guide apparatus for a surgical cutting tool. The guide apparatus may be applied in various surgical operations and may be particularly well suited to operations involving the proximal or distal resection of bones for joint repair or replacement. The guide apparatus may generally provide for the alignment of a guide plane along which a bone may be cut or resected for connecting or implanting a prosthetic device. As demonstrated in various exemplary embodiments, the guide apparatus may be positioned by installing or implanting one or more alignment pins or features in connection with a bone of a patient. The guide apparatus may engage the alignment pins and position the guide plane of a surgical cutting tool along a planar surface extending through the joint. Once aligned, the cutting tool may be guided in operation to accurately remove the bone and tissue necessary to attach the prosthetic device or complete a modification to the bone.

In some implementations, the guide apparatus may include a plurality of plates arranged in parallel with a guide plane aligned with a resection surface. The plates may include opposing, bearing surfaces spaced apart over a clearance distance that defines a planar opening. In operation, a sheath may be configured to receive the surgical cutting tool and slidably engage the planar opening between the bearing surfaces within the clearance distance. The sheath may include a cylindrical portion extending along a longitudinal axis and form an interior passage extending through the cylindrical portion along the longitudinal axis. The interior passage in the sheath may receive a rotary cutting head of the surgical cutting tool and align a motion of the surgical cutting tool along the guide plane to accurately remove bone and tissue to expose the resection surface.

In various implementations, the guide apparatus may include one or more of the following features:
the sheath further comprises a bulbous portion extending outward from the cylindrical portion;
a groove is formed along a path in the bearing surface of at least one of the plates and receives the bulbous portion of the sheath;
the path of the groove extends to a perimeter edge of the at least one of the plurality of plates and the groove forms a perimeter opening that receives the bulbous portion of the sheath in the planar opening;
the groove is formed along the path through each of the bearing surfaces as a negative clearance profile that is complementary to a rounded exterior profile of the bulbous portion;
the bulbous portion is spherical and the groove forms a spherical opening swept along the path that receives the bulbous portion in a clearance fit configuration;
the bulbous portion slides along the path and is axially constrained translationally to the path of the groove
the cylindrical portion slides between the bearing surfaces and is rotationally constrained along the longitudinal axis;
the rotary cutting head rotates about the longitudinal axis and the cutting head is rotationally constrained to the sheath, such that the sheath and the cutting head rotate synchronously within the planar opening;
the rotary cutting head slidably engages the interior passage of the sheath along the longitudinal axis;
the plurality of plates form a profile cutting guide along which a cutting depth of the rotary cutting head is limited along the longitudinal axis;
the cutting depth is limited along the longitudinal axis by a translational interference between a positive stop in connection with the rotary cutting head and profile feature of the plurality of plates;
the profile feature is a profile edge of at least one of the plurality of plates, or a profile cutting path formed by a groove between the bearing surfaces;
the cutting head comprises at least one of a burr, rasp, drill, router bit, and an end mill;
at least one connecting spacer is disposed between the plates;
the connecting spacer is disposed centrally between the plates and occludes a portion of the path of the groove; and/or
the spacer is a column that connects the plurality of plates and affixes the parallel arrangement with the guide plane and the clearance distance defining the planar opening.

In some implementations, the guide apparatus may include a plurality of plates arranged in parallel that form opposing bearing surfaces spaced apart over a clearance distance defining an opening. A sheath may form an elongated body extending along a longitudinal axis and may include a bulbous portion protruding from the elongated body. The sheath may form an interior passage extending though the elongated body along the longitudinal axis. The interior passage of the sheath receives a cutting head of the surgical cutting tool in an operating configuration. A groove may be formed in one of the bearing surfaces of the plates. The groove may form a complimentary shape to the bulbous portion of the sheath, such that the groove is configured to receive the bulbous portion and allow the sheath to slide between the plates along a guide plane.

In various implementations, the guide apparatus may include one or more of the following features:
the groove forms a path along the bearing surface through which the bulbous portions slides;
the elongated body of the sheath slidably engages the opening through the clearance distance, and wherein the interior passage of the sheath receives the cutting head of the surgical cutting tool in an operating configuration;
the cutting tool is a rotary cutting tool comprising a cross section that extends perpendicular to the longitudinal axis and forms a mating profile, wherein the interior passage slidably receives the cutting head along the longitudinal axis and rotationally engages the mating profile; and/or the mating profile forms a polygonal shape that slidably extends through the interior passage along the longitudinal axis and rotationally engages the interior passage along two or more sides.

In some implementations, the disclosure may provide for a method of guiding a surgical tool within a guide apparatus. The method may include receiving a cutting head of a surgical tool within an interior passage formed through a sheath. An elongated body of the sheath may be guided in an opening between parallel guide plates that are spaced apart over a clearance distance and aligned with a guide plane. The sheath may be guided between the parallel guide plates through a groove formed along a path between the parallel guide plates. A rotation of the cutting head of the surgical tool may result in a synchronous rotation of the sheath with the cutting head within the opening formed between the parallel guide plates. In some embodiments, the synchronous rotation of the cutting head and the sheath within the opening restricts a cutting path of the cutting head along the guide plane. Additionally, the guide apparatus may include an alignment feature in connection with the plurality of plates. The alignment feature may form locating apertures that receive alignment pins that extend along the guide plane.

These and other features, objects and advantages will become apparent upon reading the following description thereof together with reference to the accompanying drawings.

DETAILED DESCRIPTION

Figure 1A:
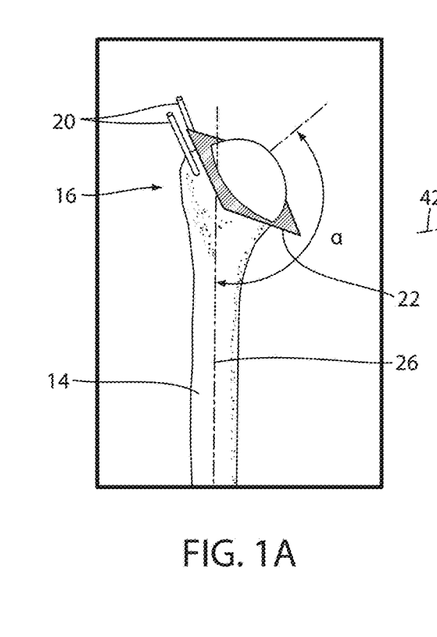
FIG. 1A is an exemplary depiction of a proximal or distal end portion of a bone demonstrating alignment pins positioned parallel to a resection plane.
Figure 1B:
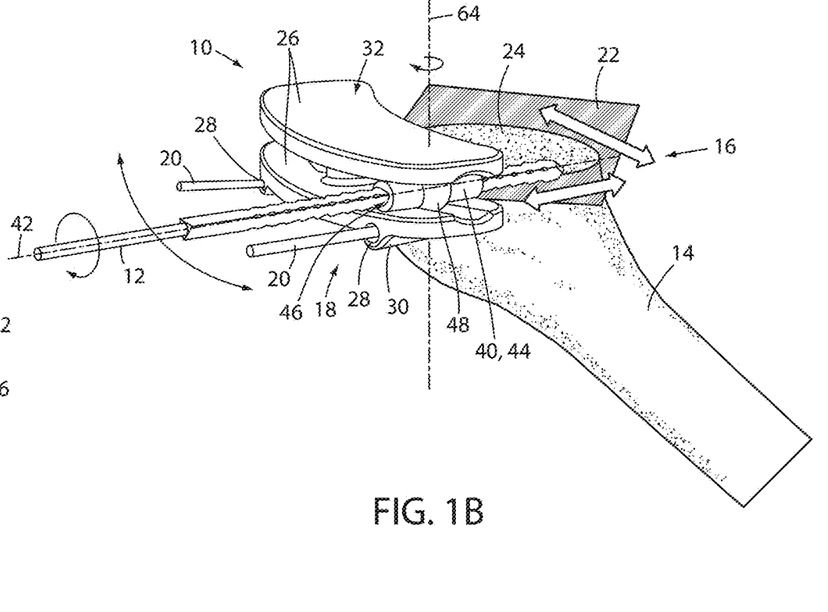
FIG. 1B is a representative projected view of a guide apparatus for a surgical cutting tool aligned with a bone to form a resection surface.

Referring to FIGS. 1A and 1B, the disclosure generally provides for a guide apparatus 10 and method for utilizing a surgical cutting tool 12 in order to accurately cut or resection a bone 14 for arthroplasty. In various implementations, the surgical cutting tool 12 may include a cutting head in the form of a burr, rasp, drill, router bit, and/or an end mill. As demonstrated in FIG. 1A, a representative depiction of the bone 14 demonstrates an end portion 16, which may correspond to a proximal or distal end portion that may form joints of a patient. In various implementations, an alignment feature 18 of the guide apparatus 10 may engage one or more alignment pins 20 that may be connected to or implanted within the bone 14. The engagement of the alignment feature 18 with the alignment pins 20 may align a guide plane 22 of the guide apparatus 10 with a resection surface 24, such that the guide apparatus 10 may limit or control the motion of the surgical cutting tool 12 along a cutting angle α defined relative to a longitudinal axis 26 of the bone 14. Accordingly, the guide apparatus 10 may provide for the alignment of the surgical cutting tool 12, such that the resection surface 24 may be exposed by removing bone and tissue from the end portion 16 to effectively promote the successful repair or replacement of a portion or segment of the bone 14. Though discussed in reference to the end portion 16 of the bone 14 in the exemplary embodiments, the guide apparatus 10 may similarly be applied to accurately align the surgical cutting tool 12 with the various portions of the bone 14 or tissue.

In various embodiments, the guide apparatus 10 may include a plurality or pair of alignment plates 26 that may be in connection with the alignment feature 18. As demonstrated, the alignment feature 18 may correspond to one or more guide apertures 28 configured to receive the alignment pins 20 and position the guide plane 22 of the guide apparatus 10 along the resection surface 24. In various implementations, the guide apertures 28 may be integrally formed as embossed ridges 30 protruding from an exterior surface 32 of one of the alignment plates 26. The guide apertures 28 may similarly be connected to the alignment plates 26 or various portions of the guide apparatus 10 as one or more sleeves or support structures providing for the guide apertures 28 to mate with the alignment pins 20 for alignment with the guide plane 22.

Figures 2A, 2B:
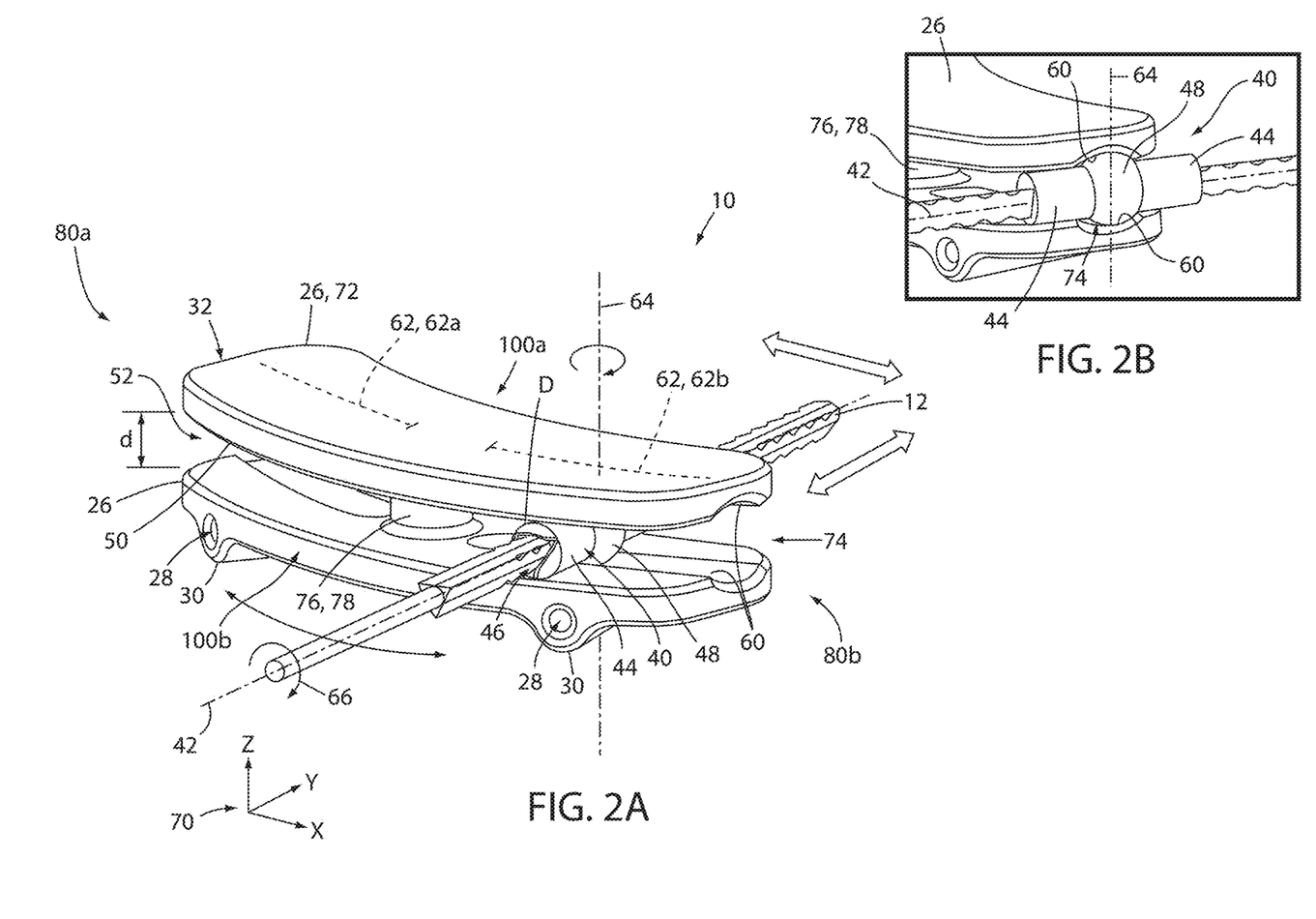
FIG. 2A is a projected assembly view of a guide apparatus for a surgical cutting tool.
FIG. 2B is a detailed projected view of a sheath being inserted between guide plates of a guide apparatus.

Referring now to FIGS. 1B, 2A, and 2B, in various embodiments, the guide apparatus 10 may include a sheath 40 having an elongated body extending along a longitudinal axis 42. The elongated body may correspond to a cylindrical portion 44 with an interior passage 46 formed therethrough along the longitudinal axis 42. A bulbous portion may protrude or extend outward from the cylindrical portion 44 and may correspond to a spherical portion 48. The bulbous or spherical portion 48 may be positioned centrally along a length of the cylindrical portion 44, such that the cylindrical portion 44 extends outward from the spherical portion 48 along the longitudinal axis 42 on opposing sides of the spherical portion 48.

The spaced configuration of the alignment plates 26 may provide for a separated parallel arrangement of opposing bearing surfaces 50 formed between the alignment plates 26. The bearing surfaces 50 of the alignment plates 26 may orient the guide plane 22 relative to the resection surface 24 and may be separated over a clearance distance d forming a planar opening 52 or alignment opening. The planar opening 52 or alignment opening may be sufficiently proportioned to provide a clearance fit to receive a height of the cylindrical portion 44 between the bearing surfaces 50. As discussed herein, a clearance fit may correspond to a free running, close running, or sliding fit between the bearing surfaces 50 and an exterior wall of the cylindrical portion 44. For example, a clearance fit may provide for the clearance distanced to exceed a nominal diameter D of the cylindrical portion 44 by approximately 25 to 500 microns (e.g., approximately, 0.001 to 0.020 inches). Though specific ranges are discussed in the exemplary embodiments for the clearance fit, the specific proportions of the sheath 40 and the planar opening 52 may vary based upon the intended application and specified tolerances for the guide apparatus 10.

The bulbous or cylindrical portion 44 of the sheath 40 may be configured to engage a groove 60 formed within at least one of the bearing surfaces 50. The groove 60 may extend along each of the bearing surfaces 50 along a path 62, which may be mirrored across the bearing surfaces 50. In this configuration, a spherical exterior surface of the spherical portion 48 may engage a negative swept, spherical opening formed along the path 62 between or along the bearing surfaces 50. Accordingly, the spherical portion 48 of the sheath 40 may slide within the grooves 60 formed in the bearing surfaces 50, such that the sheath 40 is translationally constrained to slide along the path 62 of the grooves 60. The engagement of the bulbous or spherical portion 48 of the sheath 40 with the groove 60 in combination with the engagement of the cylindrical portion 44 between the bearing surfaces 50 may restrict the motion of the sheath 40 to translation along the path 62, rotation about a pivotal axis 64 of the spherical portion 48, and rotation 66 about the longitudinal axis 42. Accordingly, the movement of the surgical cutting tool 12 may be limited as a result of the engagement of the sheath 40 within the planar alignment opening 52 formed by the guide apparatus 10.

Referring now to FIGS. 1B, 2A, 2B, 3A, 3B, 4A, and 4B, various aspects of the guide apparatus 10 are discussed in further detail. As shown in FIG. 2A, a coordinate system 70 is shown with a Y-axis aligned parallel to the longitudinal axis 42 and an X-Y plane aligned parallel to the guide plane 22. The coordinate system 70 and corresponding X, Y, and Z axes may be referred to throughout the description to clearly define the constraints to or motion of the rotation and translation of the surgical cutting tool 12 relative to the alignment plates 26 and various additional features of the guide apparatus 10.

As shown in FIG. 2B, the grooves 60 may extend along the path 62 to a perimeter edge 72 of the alignment plates 26. The intersection of the openings between the bearing surfaces 50 formed by the grooves 60 may form a perimeter opening 74 that provides a clearance fit to receive the bulbous or spherical portion 48 of the sheath 40 within the grooves 60. The perimeter opening 74 may provide for the assembly of the sheath 40 with the guide or alignment plates 26, such that the guide apparatus 10 maybe easily assembled, even with the alignment plates 26 connected to the alignment pins 20 via the guide apertures 28. The separation and alignment of the alignment plates 26 may be provided by one or more connecting portions 76, which may correspond a connecting column 78 or spacers in connection with each of the alignment plates 26. As shown in the exemplary embodiment, the connecting column 78 is disposed centrally in the alignment opening 52 between the bearing surfaces 50. For example, the connecting column 78 may be secured to or formed integrally with the alignment plates 26 to maintain the parallel alignment of the alignment plates 26 over the clearance distance d. In this configuration, the sheath 40 may be inserted into the groove 60 via the perimeter opening 74 disposed in a first side portion 80*a* of the alignment plates 26 to access a first path 62*a* or via the perimeter opening 74 formed in a second side portion 80*b* of the alignment plates 26 to access a second path 62*b*. As shown, the first path 62*a* and the second path 62*b* are separated by the connecting column 78 and independently accessible via the first and second side portions 80*a*, 80*b* of the alignment plates 26.

Figure 3A:
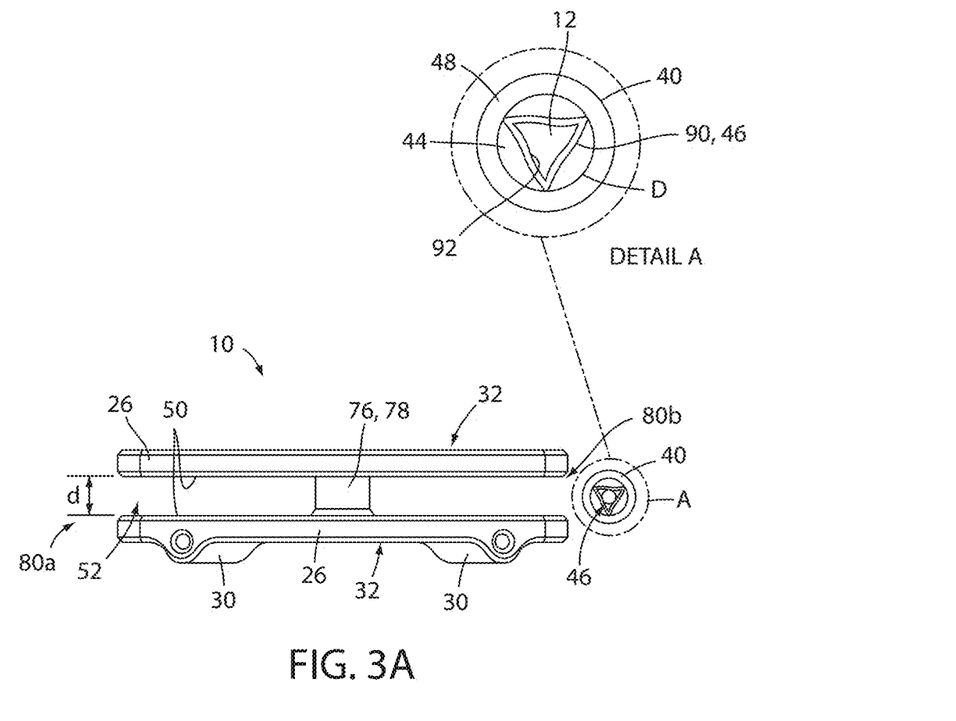
FIG. 3A is a front view of a guide apparatus.
Figure 3B:
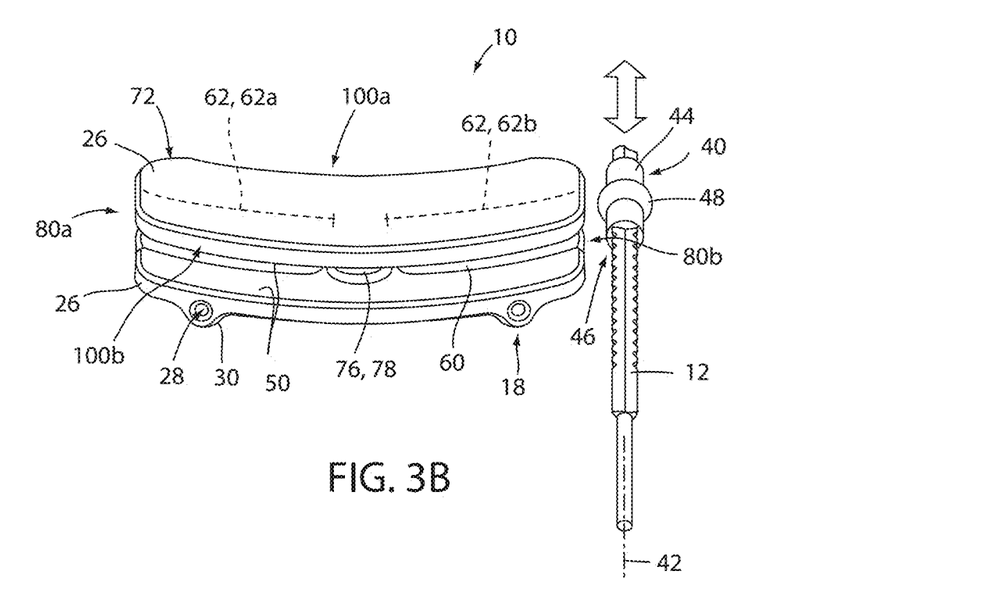
FIG. 3B is a top-front projected view of a guide apparatus.

As best shown in FIG. 3A, an interior passage 46 may be formed through the elongated body or cylindrical portion 44 of the sheath 40 along the longitudinal axis 42. In various implementations, the surgical cutting tool 12 may correspond to a rotary cutting tool configured to rotate about the longitudinal axis 42 or parallel to the Y-axis, as previously discussed. In some implementations, the interior passage 46 may form an interior receiving profile shape 90 that may complement an exterior, mating profile shape 92 formed by a cross section of the cutting tool 12 defined perpendicular to the longitudinal axis 42. In this configuration, the cutting tool 12 may slidably engage the interior passage 46 formed through the sheath 40, such that the mating profile shape 92 enters the receiving profile shape 90. Complementary mating surfaces of the receiving profile shape 90 and the mating profile shape 92 formed between an interior wall of the interior passage 46 and the cutting tool 12 may rotationally constrain the cutting tool 12 to the sheath 40 about the longitudinal axis 42. In this configuration the rotation 66 of the cutting tool 12 and the sheath 40 may synchronously occur about the longitudinal axis 42.

Additionally, the sliding engagement of the cutting tool 12 within the interior passage 46 may allow the cutting tool 12 to freely translate along the longitudinal axis 42 within the interior passage 46. In this way, the motion of the cutting tool 12 maybe limited by the constraints created among the sheath 40, the groove 60, and the bearing surfaces 50 formed between the alignment plates 26 to achieve an operating alignment of the guide plane 22. The complementary profiles shapes 90, 92 of the interior passage 46 of the sheath 40 and the cutting tool 12 are demonstrated in FIG. 3A as a fluted triangular shape. However, the profile shapes 90, 92 may correspond to various polygonal (e.g., square, hexagonal, etc.) shapes, as well as various complex shapes that may include curved segments or portions providing that the complementary profiles shapes maintain the sliding engagement along the longitudinal axis 42 and the constrained engagement rotationally about the longitudinal axis 42.

Still referring to FIGS. 2A-4B, the motion of the cutting tool 12 relative to the sheath 40 and the sheath 40 relative to the alignment plates 26 are further discussed in reference to the coordinate system 70. Specific examples of the translation of the sheath 40 along the path 62 as well as the rotation of the sheath 40 about the pivotal axis 64 are demonstrated in FIGS. 4A and 4B. As previously discussed, the movement of the sheath 40 is constrained in an upward and downward direction (e.g., along the Z-axis) by the interaction between the cylindrical portion 44 with the bearing surfaces 50. Additionally, the translation of the spherical portion 48 of the sheath 40 is constrained to the groove 60 formed along the path 62 between the bearing surfaces 50. Accordingly, the sheath 40 in connection with the cutting tool may be free to translate along the path 62 as well as rotate about the pivotal axis 64, which may vary in position based on the location of the spherical portion 48 along the path 62. In this way, the movement of the sheath 40 is constrained to translation along the path 62 as well as the rotation about the pivotal axis 64 parallel to the guide plane 22. As shown, the guide plane 22 is parallel to the X-Y plane and the pivotal axis 64 is parallel to the Z-axis of the coordinate system 70.

Figure 4A:
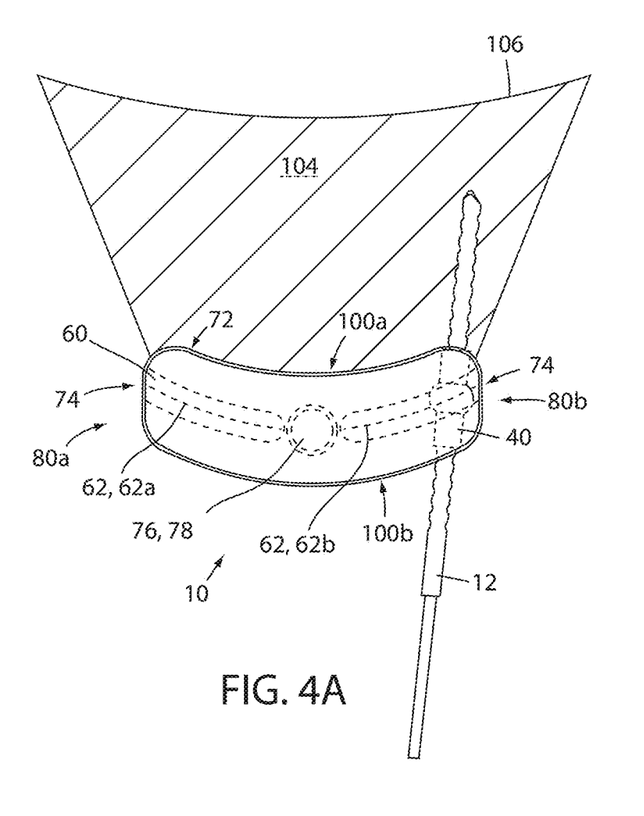
FIG. 4A is a top view of a guide apparatus demonstrating a sheath and a cutting tool in a first position.
Figure 4B:
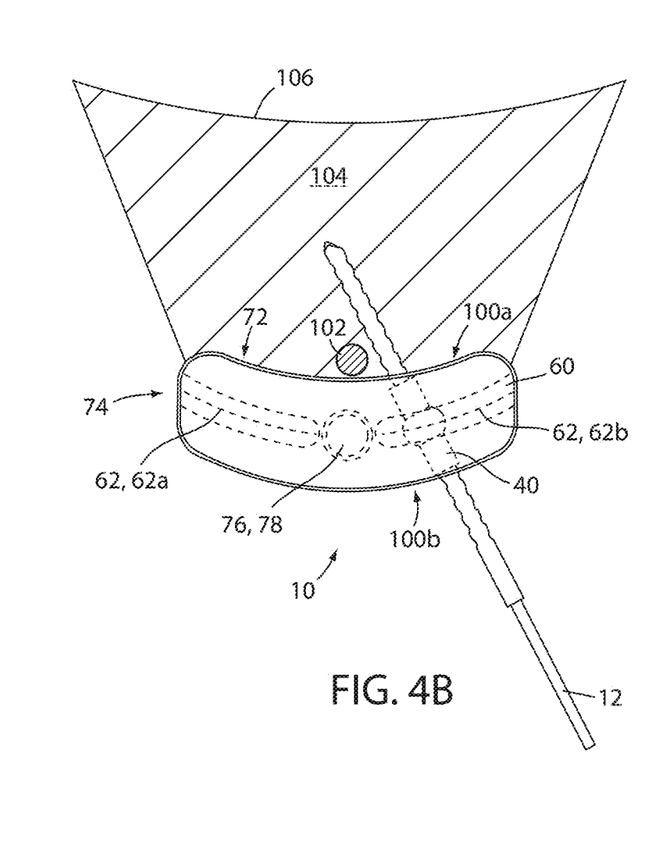
FIG. 4B is a top view of a guide apparatus demonstrating a sheath and a cutting tool in a second position.

With the sheath 40 engaged to the bearing surfaces 50 and within the groove 60, the further engagement of the cutting tool 12 within the interior passage 46 is similarly constrained in rotation but provides for an additional degree of freedom for translation of the surgical cutting tool 12 along the longitudinal axis 42. For example, the sliding engagement of the complementary receiving profile shape 90 with the mating profile shape 92 allows the cutting tool 12 to translate within the interior passage 46 of the sheath 40. Additionally, in implementations wherein the cutting tool 12 corresponds to a rotary cutting tool, the rotation about the longitudinal axis 42 may be freely provided by the guide apparatus 10. In this way, the guide apparatus 10 may provide for the translation along the longitudinal axis 42, rotation about the pivotal axis 64 and the longitudinal axis 42 while limiting the movement of the cutting tool 12 to that along the guide plane 22. In this way, the guide apparatus 10 may provide for the accurate and effective alignment of the cutting tool 12 with the resection surface 24.

In general, the materials utilized for each of the components of the guide apparatus 10 and the surgical cutting tool 12 may be selected to optimize operation of the guide apparatus 10. For example, the sheath 40 may be formed of a material at least as hard as the cutting tool 12. Further, the alignment plates 26 may be formed of a material that is softer or that has a lower hardness than the sheath 40. The similar hardnesses of the cutting tool 12 and the sheath 40 may prevent wear that may result from high speed synchronous rotation of the cutting tool 12 about the longitudinal axis 42, which may be applied in combination with the translation of the cutting tool 12 within the interior passage 46. Further, the application of a material with a decreased hardness for the alignment plates 26 or portions forming the bearing surfaces 50 and the groove 60 may prevent galling or wear that may otherwise result from a high speed rotation of the sheath 40. Accordingly, the alignment plates 26 or at least the bearing surfaces 50 and the surfaces forming the groove 60 may be formed of, coated with, or lined with materials with lower hardnesses than the sheath 40. For example, the sheath 40 and the cutting tool 12 may be of various forms of hardened steel or tool steel. The alignment plates 26, associated bearing surfaces 50, and/or the surface of the groove 60 may be formed of materials with a lower hardness than the cutting tool 12 and the sheath 40 (e.g., a polymer or low hardness metal with a Mohs scale hardness less than 4).

Referring to FIGS. 4A and 4B, a top view of the alignment plates 26 demonstrates the perimeter edge 72. As shown, a front profile edge 100*a* and a rear profile edge 100*b* extend concentrically along the path 62 of the groove 60. The front profile edge 100*a* may form a rounded contour that may extend partially around the end portion 16 of the bone 14. In such cases, the rounded contour of the front profile edge 100*a* may improve accessibility to the bone 14, particularly in cases where one or more occlusions 102 may be located in a working range of the cutting tool 12. For example, in order to perform some surgical operations, the front profile edge 100*a* of the alignment plates 26 may partially wrap around a tendon or connecting tissue represented in FIG. 4B as an occlusion 102. In such cases, the guide apparatus 10 may implement the connecting column 78 centrally located along the path 62, such that the connecting column 78 can be aligned with the connecting tissue represented by the occlusion 102. In this way, the connecting column 78 may serve as a physical barrier or stop along the path 62 that may be utilized to guide the motion of the surgical cutting tool 12 within the sheath 40 to prevent cutting the tissue corresponding to the occlusion 102. In this way, the guide apparatus 10 may align the cutting tool 12 with the resection surface 24 while providing a physical stop in the form of the connecting column 78 that may assist an operator (e.g., a surgeon, doctor, etc.) in avoiding contact with the tissue or tendon represented by the occlusion 102.

The rear profile edge 100*b* may follow the rounded concentric profiles of the front profile edge 100*a* and the path 62. In this configuration, a reach or extent 106 of the working range 104 may generally correspond to the curvature of the path 62. Additionally, in some embodiments, the rear profile edge 100*b* may be implemented as a profile cutting guide 108 that may limit the extent 106 of the working range 104 of the surgical cutting tool 12 to a profile cutting shape or profile depth of cut as further discussed in reference to FIGS. 5A, 5B, 6, and 7. The depth of the cut may correspond to a plunging depth of the cutting tool 12 in and out of the interior passage 46 of the sheath 40, which may correspond to the extent that the cutting tool 12 penetrates the bone 14 or tissue in the working range 104. Though different configurations of the guide apparatus 10 are discussed in various figures of the disclosure, like reference numerals may be referenced in relation to similar elements for clarity. Additionally, variations among the several embodiments disclosed in the application may be combined in various ways without departing from the spirit of the disclosure.

Figure 5A:
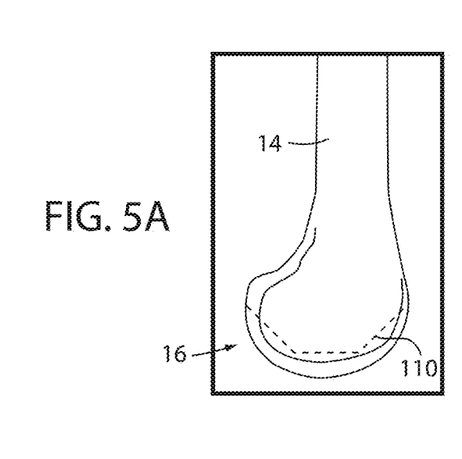
FIG. 5A is a representation of a bone demonstrating a resection pattern for arthroplasty.
Figure 5B:
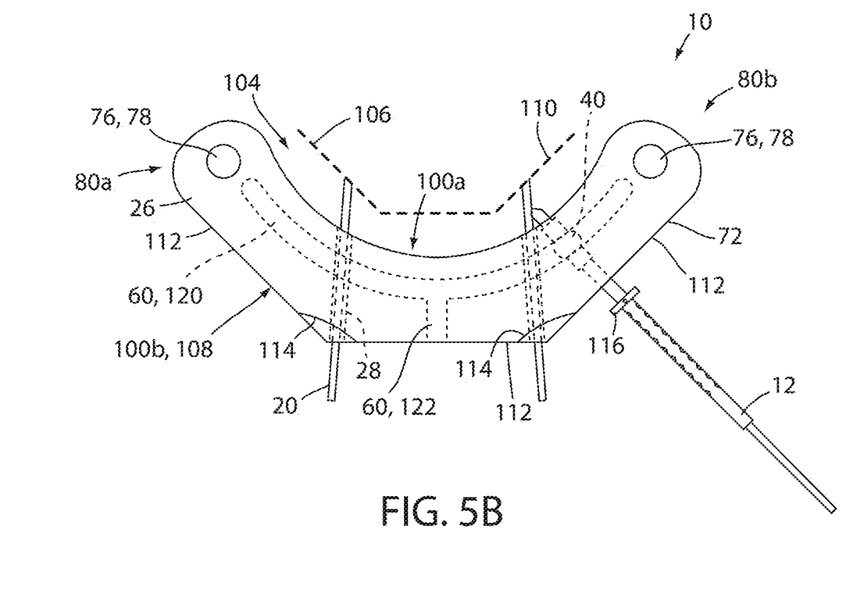
FIG. 5B is a top view of a guide apparatus demonstrating a profile cutting guide feature fora surgical cutting tool.
Figure 6:
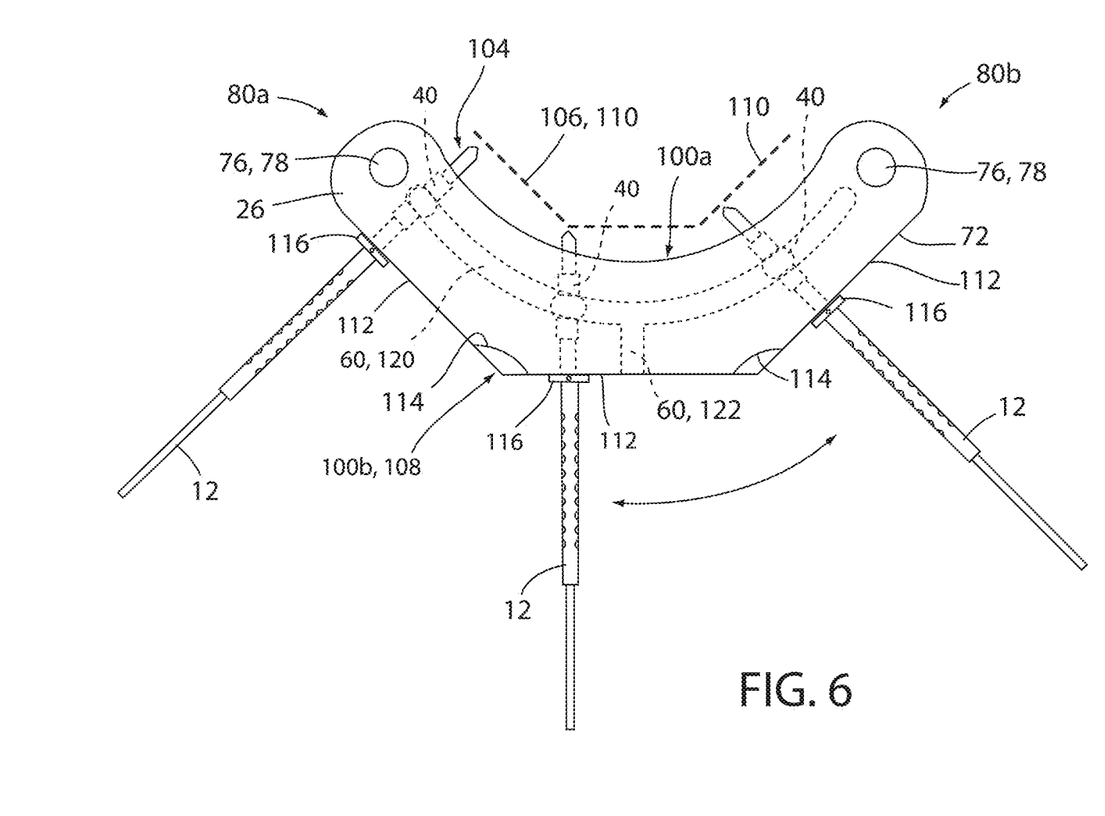
FIG. 6 is a top view demonstrating a guide apparatus comprising a profile cutting guide feature demonstrating a surgical cutting tool in multiple positions.

Referring now to FIGS. 5A-5B and 6, an implementation of the guide apparatus 10 is shown demonstrating an angular cutting implementation of a profile cutting guide 108. As shown in FIG. 5A, in some operations, the profile cutting guide 108 of the guide apparatus 10 may be implemented to section or create a pocket/groove in the end portion 16 along an angled, faceted, or a generally contoured profile 110. The contoured profile 110 may be provided by controlling a cutting depth of the cutting tool 12 with the profile cutting guide 108. As shown in FIG. 5B, the profile cutting guide 108 comprises a plurality of linear segments 112 that intersect at cutting angles 114 that match the contoured profile 110. In order to limit the travel of the cutting tool 12 along the longitudinal axis 42, a stop collar 116 or positive stop may be positioned in connection with the cutting tool 12, such that the extent 106 of the working range 104 is limited along the longitudinal axis 42 by the interference between the stop collar 116 and the profile cutting guide 108 extending along the rear profile edge 100*b* of the alignment plates 26. In this way, the profile cutting guide 108 may control the reach or extent 106 of the working range 104 of the cutting tool 12, such that the contoured profile 110 of the cutting depth can conform to the shape of the profile cutting guide 108 as depicted in FIG. 6.

Still referring to FIGS. 5A, 5B, and 6, the implementation of the guide apparatus 10 provides for the connecting portions 76 in the form of two connecting columns 78 that may be positioned near the first side portion 80*a* and the second side portion 80*b*. Similar to other implementations of the guide apparatus 10, the groove 60 is formed between the alignment plates 26. In the example shown in FIGS. 5A, 5B, and 6, a path 120 is located between the connecting columns 78 and extends to the perimeter edge 72. More specifically, the path 120 extends to the rear profile edge 100*b* of the alignment plates 26 via an intermediate access path 122. In this configuration, the groove 60 formed in the bearing surfaces 50 of the alignment plates 26 extends along the path 120 and the intermediate access path 122. At the intersection of the intermediate access path 122 and the rear profile edge 100*b*, the perimeter opening 74 may be formed by the groove 60 and provide for the spherical portion 48 of the sheath 40 to engage the groove and slide along the intermediate access path 122 to the path 120. In this configuration, the sheath 40 may be slidably bound to translate along the path 120 and the intermediate access path 122 in an assembled configuration. Though the path 120 and the intermediate access path 122 are discussed in reference to the profile cutting guide 108 and corresponding implementations of the guide apparatus 10, the path 120 and the intermediate access path 122 may similarly be implemented in the guide apparatus previously discussed in reference to FIGS. 1-4. Similarly, the connecting columns 78 disposed proximate to the first side portion 80a and the second side portion 80b may be implemented in various embodiments of the guide apparatus 10.

Figure 7:
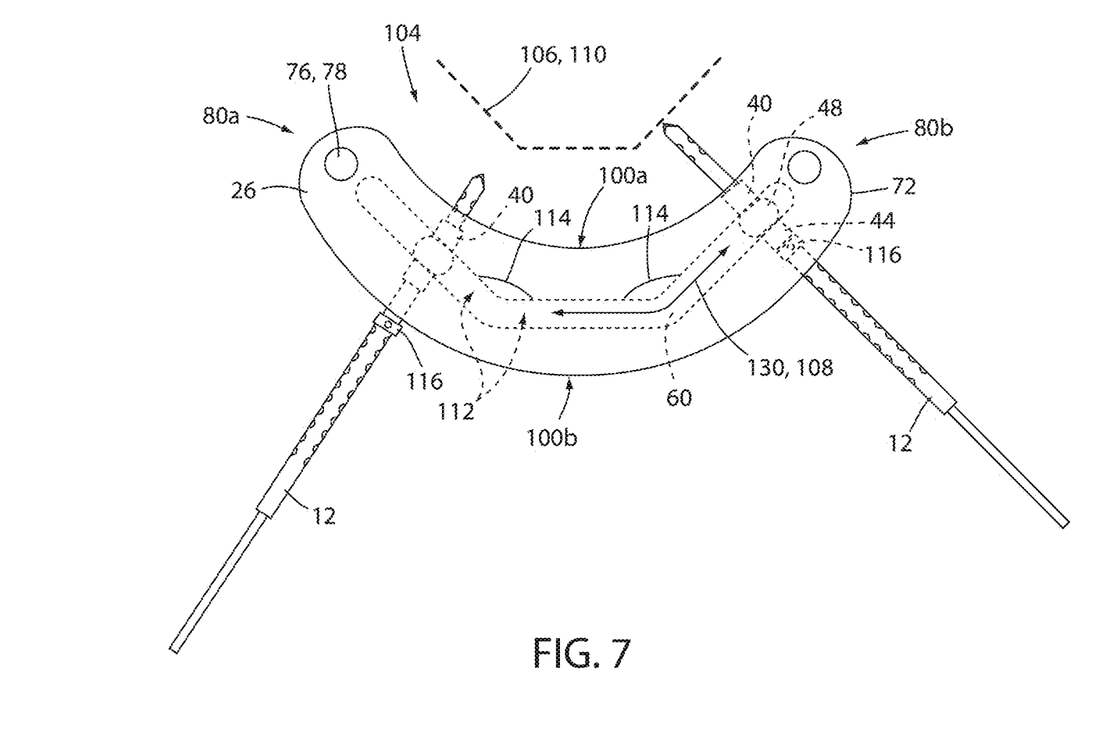
FIG. 7 is a top view of a guide apparatus comprising a profile cutting guide feature in accordance with the disclosure.

Referring now to FIG. 7, the guide apparatus 10 may incorporate the profile cutting guide 108 by limiting the cutting depth of the cutting tool 12 similarly with a stop collar 116 or positive stop that engages a profile cutting path 130 that may be formed by the groove 60 between the bearing surfaces 50. In some implementations, the stop collar 116 may be proportioned to conform to the height or diameter of the cylindrical portion 44 of the sheath 40. In this configuration, the stop collar 116 may slide between the bearing surfaces 50 similar to the cylindrical portion 44 but may limit the travel of the surgical cutting tool 12 along the longitudinal axis 42 based on the interference between the stop collar 116 and the sheath 40. In such implementations, the rear profile edge 100b of the alignment plates 26 may not necessarily correspond to the profile cutting guide 108. For example, in some implementations, the profile cutting path 130 of the groove 60 may correspond to the contoured profile 110 defining the cutting depth or extent 106 of the working range 104 of the cutting tool 12. As shown in FIG. 7, the bulbous or spherical portion 48 of the sheath 40 may freely translate along the profile cutting path 130, which may guide the translational movement of the cutting tool 12. Additionally, the interference between the stop collar 116 and the sheath 40 may limit the cutting depth of the cutting tool 12 to correspond to the contoured profile 110. In this way, the guide apparatus 10 may provide for yet another optional solution to control the contoured cutting profile 110 of the cutting tool 12.

Still referring to FIG. 7, in some implementations, the profile cutting path 130 may incorporate the intermediate access path 122 as previously discussed in reference to FIGS. 5A, 5B, and 6. In the exemplary embodiment shown in FIG. 7, the profile cutting path 130 does not provide for the perimeter opening 74 and remains bound between the alignment plates 26. In such implementations, the sheath 40 may be installed with the cylindrical portion 44 extended into the groove 60 during a manufacturing or assembly operation of the alignment plates 26. Additionally, in some cases, one or more of the connecting portions 76 (e.g., the connecting column 78) that interconnect the alignment plates 26 may be connected via one or more fasteners (e.g., screws, nuts and bolts, etc.), such that the alignment plates 26 may be separated and the bulbous or spherical portion 48 of the sheath 40 may be inserted into the groove 60 prior to affixing the alignment plates 26 together in the assembled configuration.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents

What is claimed:

1. A guide apparatus for a surgical cutting tool comprising:
   a plurality of plates arranged in parallel with a guide plane, the plurality of plates comprising opposing bearing surfaces spaced apart over a clearance distance defining a planar opening;
   a sheath comprising a cylindrical portion extending along a longitudinal axis, wherein the sheath forms an interior passage extending through the cylindrical portion along the longitudinal axis; and
   wherein the cylindrical portion of the sheath slidably engages the planar opening through the clearance distance, wherein the interior passage of the sheath receives a rotary cutting head of the surgical cutting tool and the rotary cutting head slidably engages the interior passage of the sheath along the longitudinal axis in an operating configuration, and wherein the rotary cutting head rotates about the longitudinal axis and the rotary cutting head is rotationally constrained to the sheath, such that the sheath and the rotary cutting head rotate synchronously within the planar opening.

2. The guide apparatus according to claim 1, wherein the sheath further comprises a bulbous portion extending outward from the cylindrical portion.

3. The guide apparatus according to claim 2, wherein a groove is formed along a path in the bearing surface of at least one of the plurality of plates and receives the bulbous portion of the sheath.

4. The guide apparatus according to claim 3, wherein the path of the groove extends to a perimeter edge of the at least one of the plurality of plates and the groove forms a perimeter opening that receives the bulbous portion of the sheath in the planar opening.

5. The guide apparatus according to claim 3, wherein the groove is formed along the path through each of the bearing surfaces as a negative clearance profile that is complementary to a rounded exterior profile of the bulbous portion.

6. The guide apparatus according to claim 3, wherein the bulbous portion is spherical and the groove forms a spherical opening swept along the path that receives the bulbous portion in a clearance fit configuration.

7. The guide apparatus according to claim 3, wherein the bulbous portion slides along the path and is constrained translationally to the path of the groove.

8. The guide apparatus according to claim 1, wherein the cylindrical portion slides between the bearing surfaces and is rotationally constrained to the rotary cutting head along the longitudinal axis.

9. The guide apparatus according to claim 1, wherein the plurality of plates form a profile cutting guide along which a cutting depth of the rotary cutting head is limited along the longitudinal axis.

10. The guide apparatus according to claim 1, wherein the rotary cutting head comprises at least one of a burr, a rasp, a drill, a router, and an end mill.

11. The guide apparatus according to claim 1, further comprising at least one connecting spacer disposed between the plurality of plates.

12. The guide apparatus according to claim 11, wherein the at least one connecting spacer is disposed centrally between the plurality of plates and occludes a portion of a path of a groove.

13. The guide apparatus according to claim 11, wherein the at least one connecting spacer is a column that connects the plurality of plates and affixes the parallel arrangement with the guide plane and the clearance distance defining the planar opening.

14. The guide apparatus according to claim 1, wherein the sliding engagement of the cutting head within the interior passage of the sheath varies a depth of cut of the cutting tool.

15. A guide apparatus for a surgical cutting tool comprising a cutting head, the guide apparatus comprising:
a plurality of plates arranged in parallel, the plates comprising opposing bearing surfaces spaced apart over a clearance distance defining an opening;
a sheath comprising an elongated body extending along a longitudinal axis and a bulbous portion protruding from the elongated body, wherein the sheath slidably engages the opening through the clearance distance and forms an interior passage extending through the elongated body along the longitudinal axis, wherein the interior passage of the sheath receives the cutting head of the surgical cutting tool in an operating configuration, wherein the interior passage slidably receives the cutting head along the longitudinal axis and the sliding engagement of the cutting head within the interior passage varies a depth of cut of the cutting head and the cutting head is rotationally constrained to the sheath about the longitudinal axis; and
wherein a groove is formed in the bearing surface of at least one of the plurality of plates and receives the bulbous portion of the sheath.

16. The guide apparatus according to claim 15, wherein the groove forms a path along the bearing surface along which the bulbous portion slides.

17. The guide apparatus according to claim 15, wherein the surgical cutting tool is a rotary cutting tool comprising a cross section that extends perpendicular to the longitudinal axis and forms a mating profile.

18. The guide apparatus according to claim 17, wherein the interior passage rotationally engages the mating profile of the rotary cutting tool.

19. The guide apparatus according to claim 18, wherein the mating profile forms a polygonal shape that slidably extends through the interior passage along the longitudinal axis and rotationally engages the interior passage along two or more sides.

20. A method of guiding a surgical tool within a guide apparatus, the method comprising:
receiving a cutting head of the surgical tool within an interior passage formed through a sheath;
guiding an elongated body of the sheath in an opening between parallel guide plates spaced apart over a clearance distance along a guide plane;
guiding the sheath between the parallel guide plates along a groove formed along a path between the parallel guide plates;
synchronously rotating the cutting head of the surgical tool and the sheath within the opening between the parallel guide plates; and
adjusting a cutting depth of the cutting head relative to the sheath by sliding a length of the cutting head through the interior passage of the sheath.

21. The method according to claim 20, wherein the synchronous rotation of the cutting head and the sheath within the opening restricts a cutting path of the cutting head along the guide plane.

* * * * *